United States Patent
Lai et al.

(10) Patent No.: US 10,704,106 B2
(45) Date of Patent: Jul. 7, 2020

(54) METHODS AND KITS FOR ASSESSING THE RISK OF DEVELOPING OR DIAGNOSING ENDOMETRIAL CANCER

(71) Applicant: Chang Gung Memorial Hospital, Linkou, Taoyuan (TW)

(72) Inventors: Chyong-Huey Lai, Taoyuan (TW); Lan-Yan Yang, Taoyuan (TW); Chiao-Yun Lin, Taoyuan (TW); Angel Chao, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 104 days.

(21) Appl. No.: 15/917,458

(22) Filed: Mar. 9, 2018

(65) Prior Publication Data

US 2018/0258493 A1 Sep. 13, 2018

Related U.S. Application Data

(60) Provisional application No. 62/469,724, filed on Mar. 10, 2017.

(51) Int. Cl.
*C12Q 1/6886* (2018.01)
*C07H 21/02* (2006.01)
*C07H 21/04* (2006.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2018/0208995 A1* 7/2018 Galon .................. C12Q 1/6886

FOREIGN PATENT DOCUMENTS

| WO | WO2011/057304 A2 | 5/2011 |
|----|------------------|--------|
| WO | WO2015/128671 A1 | 9/2015 |
| WO | WO2016/025477 A1 | 2/2016 |

OTHER PUBLICATIONS

Koichi Yoneyama, et al.; "miR-200a, miR-200b and miR-429 Are Onco-miRs That Target the PTEN Gene in Endometrioid Endometrial Carcinoma"; AntiCancer Research 35: 1401-1410 (2015).

Heejeong Lee, et al.; "Expression of miRNAs and PTEN in Endometrial Specimens Ranging From Histologically Normal to Hyperplasia and Endometrial Adenocarcinoma"; Modern Pathology (2012) 25, 1508-1515.
Jiafeng Lu, et al,; "MicroRNA Heterogeneity in Endometrial Cancer Cell Lines Revealed by Deep Sequencing"; Oncology Letters 10: 3457-3465, 2015.
Yun Gao, et al.; "Diagnostic Value of Circulating miR-21: An Update Meta-Analysis in Various Cancers and Validation in Endometrial Cancer"; Sep. 15, 2016; Oncotarget, Advance Publications 2016; 15 pgs.
Liu et al., "Association of SNPs in miR-146a, miR-196a2, and miR-499 with the risk of endometrial/ovarian cancer," Acta Biochim Biophys Sin, 2015, 47(7), pp. 564-566.
Zhao et al., "TSA Suppresses miR-106b-93-25 Cluster Expression through Downregulation of MYC and Inhibits Proliferation and Induces Apoptosis in Human EMC," PLOS ONE, vol. 7, Issue 9, 12 pages.
Torres et al., "Highly Increased Maspin Expression Corresponds With Up-Regulation of miR-21 in Endometrial Cancer," International Journal of Gynecological Cancer, vol. 21, No. 1, Jan. 2011, pp. 8-14.
Dai et al., "MicroRNA-200b Is Overexpressed in Endometrial Adenocarcinomas and Enhances MMP2 Activity by Downregulating TIMP2 in Human Endometrial Cancer Cell Line HEC-1A Cells," Nucleic Acid Therapeutics, vol. 23, No. 1, 2013, pp. 29-34.
Myatt et al., "Definition of microRNAs That Repress Expression of the Tumor Suppressor Gene FOXO1 in Endometrial Cancer," American Association for Cancer Research, vol. 70, No. 1, 1 Jan. 2010, pp. 367-377.
Joshi et al., "Altered expression of microRNA-451 in eutopic endometrium of baboons (Papio anubis) with endometriosis," Human Reproduction, vol. 30, No. 12, pp. 2881-2901, 2015.
Cosar et al., "Serum microRNAs as diagnostic markers of endometriosis: a comprehensive array-based analysis," Fertility and Sterility, vol. 106, No. 2, Aug. 2016, pp. 402-409.
Ondrej Slaby et al., "Dynamic changes in microRNA expression profiles reflect progression of Barrett's esophagus to esophageal adenocarcinoma," Carcinogenesis, Mar. 16, 2015, pp. 521-527, vol. 36, No. 5, Oxford University Press.

* cited by examiner

*Primary Examiner* — Sean McGarry
(74) *Attorney, Agent, or Firm* — Pilloff Passino & Cosenza LLP; Sean A. Passino; Rachel K. Pilloff

(57) ABSTRACT

Methods for diagnosing or predicting the risk of developing endometrial cancer in a subject in need of such diagnosis or risk prediction are provided, comprising measuring the expression level of at least two miRNAs disclosed herein in the sample of the subject, and compared the expression level of at least two of the miRNAs in the test sample with that of the endometrial cancer-free sample. Kits for diagnosing or predicting the risk of developing endometrial cancer, containing an agent for sequencing or measuring the expression level of at least two miRNAs disclosed herein.

8 Claims, 1 Drawing Sheet
Specification includes a Sequence Listing.

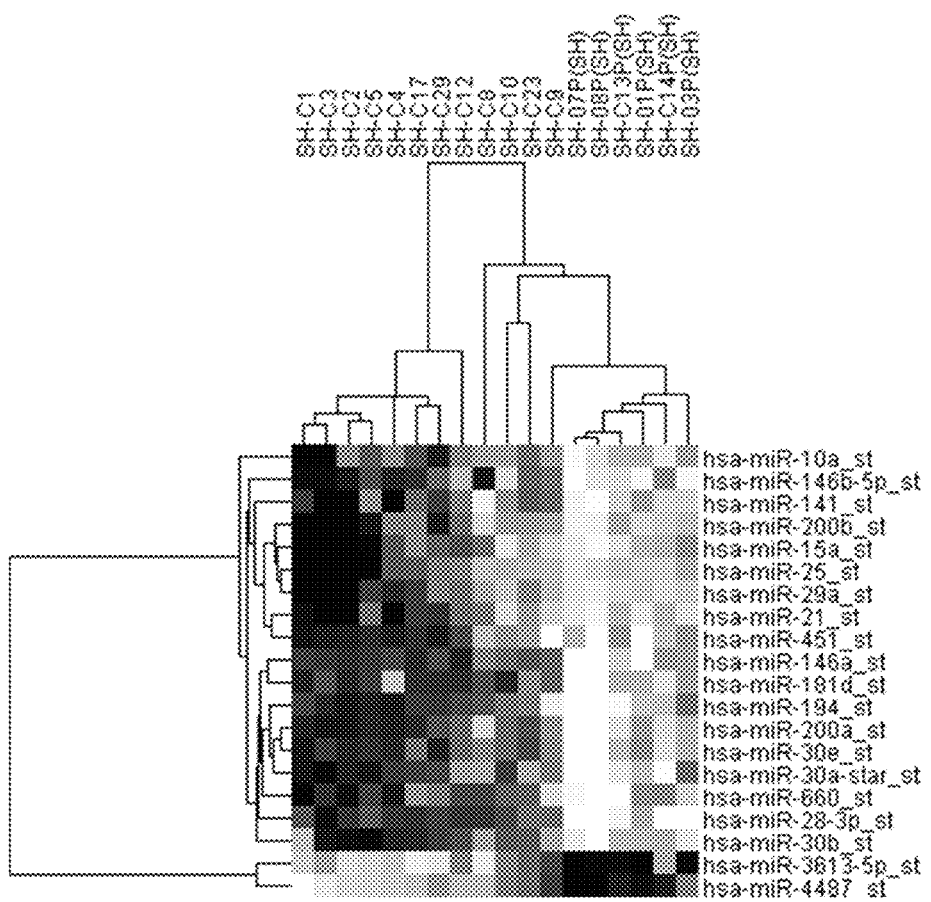

US 10,704,106 B2

METHODS AND KITS FOR ASSESSING THE RISK OF DEVELOPING OR DIAGNOSING ENDOMETRIAL CANCER

CROSS-REFERENCES TO RELATED APPLICATION

This application claims the benefit of priority from U.S. Provisional Application No. 62/469,724, filed 10 Mar. 2017, the entire content of which is incorporated herein by reference.

BACKGROUND

Endometrial cancer is the leading gynecological malignancy in industrialized countries. The World Health Organization classification categorizes endometrial hyperplasia as simple hyperplasia, complex hyperplasia without atypia, simple atypical, or complex atypical hyperplasia on the basis of architectural crowding and nuclear atypia. The severity of an endometrial hyperplasia reflects the risk of developing endometrial carcinoma. According to Kurman et al. (The behavior of endometrial hyperplasia. A long-term study of "untreated" hyperplasia in 170 patients. *Cancer* 56: 403-412), the risk of progression to carcinoma was less than 1% in simple hyperplasia. However, there are exceptions in patients with simple hyperplasia or complex hyperplasia without atypia in whom the progression to endometrial cancer occurred in a short period of time.

MicroRNAs (miRNAs) are evolutionarily conserved, non-coding RNA molecules that are usually 21-25 nucleotides in length, which function by binding to the 3'-untranslated regions (3'-UTRs) of mRNAs, where they repress protein translation or promote mRNA degradation (See Griffiths-Jones S (2004). The microRNA Registry. *Nucleic acids research* 32: D109-111). Most current studies of miRNAs are at a basic level and further work is needed to establish their clinical applications in endometrial cancer.

Cancer biomarkers for endometrial cancers, such as CA-125, have limited clinical application due to the low sensitivity and specificity of these biomarkers. Consequently, a non-invasive and convenient diagnostic method for predicting the risk of endometrial cancer and/or diagnosing endometrial cancer is needed and the present invention satisfy this and other needs.

BRIEF SUMMARY OF THE INVENTION

Accordingly, the present invention provides methods for detecting endometrial cancer or predicting the risk of developing endometrial cancer in a subject, comprising the step of measuring the expression level of at least one miRNA selected from the group consisting of miR10a, miR25, miR28-3p, miR29a, miR30a*, miR30b, miR30e, miR146a, miR146b-5p, miR451, miR660, miR3613-5p and miR4487 in the sample of the subject, where in a higher expression level of at least one of the following miRNA in the sample, relative to the expression level of at least one corresponding miRNA in an endometrial cancer-free sample, is indicative of the subject having endometrial cancer or has a risk of developing endometrial cancer: miR10a, miR25, miR28-3p, miR29a, miR30a*, miR30b, miR30e, miR146a, miR146b-5p, miR451 or miR660, and where in a lower expression level of at least one of the following miRNA in the test sample, relative to the expression level of at least one corresponding miRNA in an endometrial cancer-free sample, is indicative of the subject having endometrial cancer or has a risk of developing endometrial cancer: miR-3613-5P or miR4487.

The present invention further provides kits for detecting endometrial cancer or predicting the risk of developing endometrial cancer in a subject, comprising: an agent for sequencing or measuring the expression level of at least one miRNA in the test sample of the subject selected from the group consisting of miR10a, miR25, miR28-3p, miR29a, miR30a*, miR30b, miR30e, miR146a, miR146b-5p, miR451, miR660, miR3613-5p and miR4487.

In an exemplary embodiment, the kit further comprises a label stating that a higher expression level of at least one miRNA in the test sample, relative to the expression level of at least one corresponding miRNA in an endometrial cancer-free sample, is indicative of the subject having endometrial cancer or has a risk of developing endometrial cancer: miR10a, miR25, miR28-3p, miR29a, miR30a*, miR30b, miR30e, miR146a, miR146b-5p, miR451 or miR660, and a lower expression level of at least one of the following miRNA in the test sample, relative to the expression level of at least one corresponding miRNA in an endometrial cancer-free sample, is indicative of the subject having endometrial cancer or has a risk of developing endometrial cancer: miR-3613-5P or miR4487

Also provided are methods for identifying a test therapeutic agent to inhibit endometrial cancer cells, comprising: comprising : a) determining the level of expression of at least one miRNA selected from the group consisting of miR10a, miR25, miR28-3p, miR29a, miR30a*, miR30b, miR30e, miR146a, miR146b-5p, miR451, miR660, miR3613-5p and miR4487 prior to contacting the test therapeutic agent with one or more endometrial cancer cells; and b) determining the level of expression of at least one corresponding miRNA in step (a) after contacting the test therapeutic agent with one or more endometrial cancer cells, wherein a decrease level of expression of one of more of the following miRNAs after contacting the test therapeutic agent with one or more endometrial cancer cells relative to the expression level of the corresponding miRNA prior to contacting the test therapeutic agent with one or more endometrial cancer cells, is an indication that the test therapeutic agent is efficacious for inhibiting endometrial cancer: miR10a, miR25, miR28-3p, miR29a, miR30a*, miR30b, miR30e, miR146a, miR146b-5p, miR451 or miR660, and wherein an increase level of expression of one of more of the following miRNAs after contacting the test therapeutic agent with one or more endometrial cancer cells relative to the expression level of the corresponding miRNA prior to contacting the test therapeutic agent with one or more endometrial cancer cells, is an indication that the test therapeutic agent is efficacious for inhibiting endometrial cancer: miR3613-5p or miR4487.

Methods for determining the efficacy of a therapy for inhibiting endometrial cancer cells in a subject are also provided, said method comprising a) the level of expression of at least one miRNA selected from the group consisting of miR10a, miR25, miR28-3p, miR29a, miR30a*, miR30b, miR30e, miR146a, miR146b-5p, miR451, miR660, miR3613-5p and miR4487 in a first sample obtained from the subject prior to providing at least a portion of the therapy to the subject, and b) the level of expression of at least one corresponding miRNA in step (a) in a second sample obtained from the subject after providing at least a portion of the therapy to the subject, wherein a decrease level of expression of one of more of the following miRNAs in the second sample relative to the expression level of the corresponding miRNA in the first sample, is an indication that the therapy is efficacious for inhibiting endometrial cancer: miR10a, miR25, miR28-3p, miR29a, miR30a*, miR30b, miR30e, miR146a, miR146b-5p, miR451 or miR660, and wherein an increase level of expression of one of more of the following miRNAs in the second sample relative to the expression level of the corresponding miRNA in the first sample, is an indication that the therapy is efficacious for inhibiting endometrial cancer: miR3613-5p or miR4487.

BRIEF DESCRIPTION OF THE DRAWINGS

Illustrative embodiments of the present invention are described in detail below with reference to the following FIG.:

The sole FIG. shows hierarchical clustering analysis of miRNA expression profiles of simple hyperplasia (SH)/complex hyperplasia without atypia (CH-nonA) preceded endometrial cancer (EC) (the case group, see SH-01P (SH), SH-03P (SH), SH-07P (SH), SH-08P (SH), SH-13P (SH), SH-14P) and SH/CH-nonA without endometrial cancer (the control group, see SH-C1, SH-C2, SH-C3, SH-C4, SH-05, SH-C8, SH-C9, SH-C10, SH-C12, SH-C17, SH-C23, SH-C29). Downregulated miRNAs are shown in black color and upregulated miRNAs are shown in white color.

DETAILED DESCRIPTION OF THE INVENTION

As used herein, the articles "a" and "an" refer to one or more than one (i.e., at least one) of the grammatical object of the article.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"Patient" or "subject" as used herein refers to a mammalian subject diagnosed with or suspected of having or has a risk of developing endometrial cancer. Exemplary subjects may be humans, apes, dogs, pigs, cattle, cats, horses, goats, sheep, rodents and other mammalians that can develop endometrial cancer.

As used herein interchangeably, a "microRNA," "miR," or "miRNA" refers to the unprocessed precursor) or processed (e.g., mature) RNA transcript from a miR gene. MicroRNAs are endogenous non-coding single-stranded RNAs that negatively regulate gene expression in eukaryotes and constitute a novel class of gene regulators (Chua, et al. (2009) Curr. Opin. Mol. Ther. 11:189-199). Individual miRNAs have been identified and sequenced in different organisms, and they have been given names. Names of miRNAs and their sequences are provided herein.

All numbers herein may be understood as modified by "about." As used herein, the term "about," when referring to a measurable value a temporal duration and the like or a range, is meant to encompass variations of ±10%, preferably ±5%, more preferably ±1%, and even more preferably ±0.1% from the specified value, as such variations are appropriate to expression of miRNA level unless otherwise specified.

A "higher" or a "lower" miRNA expression is a relative term and can be determined by comparison of the miRNA expression level in the test sample to that from a referenced pool of subjects known to be endometrial cancer free (i.e., control subjects).

The term "sample" as used herein refers to a sample that comprises a miRNA. The sample can be utilized for the detection of the presence and/or expression level of a miRNA of interest. Any cell, group of cells, cell fragment, or cell product can be used with the methods of the presently claimed subject matter, although biological fluids and organs that would be predicted to contain differential expression of miRNAs as compared to normal controls are best suited. In some embodiments, the sample is a relatively easily obtained, such as for example blood or a component thereof. Non limiting examples of the sample include body fluid (e.g. serum or blood), cells (e.g., blood cells or endometrial cells) and tissue (endometrium biopsy).

In other embodiments, a threshold degree of change in the level of a prognostic or diagnostic miRNA level(s) can be established, and the degree of change in the level of the indicator in a patient's sample can simply be compared to the threshold degree of change in the level. A preferred threshold change in the level for miRNA level(s) of the presently disclosed subject matter is about 5%, about 10%, about 15%, about 20%, about 25%, about 30%, about 50%, about 60%, about 75%, about 100%, and about 150%.

Measuring the level of miRNA expression refers to quantifying the amount of miRNA present in a sample. Measuring the expression level of a specific, or any miRNA, can be achieved using any method known to those skilled in the art or described herein, such as by real-time PCR, Northern blot analysis. Measuring the expression level of miRNA includes measuring the expression of either a mature form of miRNA or a precursor form that is correlated with miRNA expression.

In a particular embodiment, the level of at least one miRNA is quantified using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

In some embodiments, use of a microarray is desirable. A microarray is a microscopic, ordered array of nucleic acids, proteins, small molecules, cells or other substances that enables parallel analysis of complex biochemical samples. The technique provides many oligonucleotides or polynucleotides with known sequence information as probes to find and hybridize with the complementary strands in a sample to thereby capture the complementary strands by selective binding. The probe comprises an oligonucleotide or a polynucleotide sequence that is complementary, or essentially complementary, to at least a portion of the target miRNA sequence. "Complementary" refers to the broad concept of sequence complementarity between regions of two nucleic acid strands. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

Microarray analysis of miRNAs, for example, can be accomplished according to any method known in the art. In one embodiment, RNA is extracted from a cell such as white blood cell or a sample, the small RNAs (18-26-nucleotides) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. With regard to miRNAs disclosed herein, the probe can be 100% complementary with the target miRNA or polynucleotide sequence. However, the probe need not necessarily be completely complementary to the target polynucleotide along the entire length of the target polynucleotide so long as the probe can bind the target polynucleotide with specificity and capture it from the sample.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miRNA, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, include, but are not limited to, via agarose gel electrophoresis, the use of SYBR Green (a double stranded DNA dye), and the use of a fluorescent reporter probe.

The identification of miRNAs that are differentially expressed in endometrial cancer and endometrial cancer free subjects, allows the use of this information in a number of ways. For example, a particular treatment regime may be evaluated (e.g., to determine whether a therapy is effective in a subject with endometrial cancer). Similarly, these miRNA expression profiles allow screening of drug candidates that suppress miRNA expression in endometrial cancer or convert a poor prognosis profile to a better prognosis profile. The diagnosis of endometrial cancer may be done or confirmed by comparing the miRNA expression level in a test sample with known expression profiles from non-endometrial cancer samples. Furthermore, multiple determinations of one or more diagnostic or prognostic miRNA levels can be made, and a temporal change in the levels can be used to determine a diagnosis, prognosis or relapse. For example, specific miRNA level(s) can be determined at an initial time, and again at a second time. In some embodiments, an increase in the miRNA level(s) from the initial time to the second time can be diagnostic of the endometrial cancer, or a given prognosis. Likewise, a decrease in the miRNA level(s) from the initial time to the second time can be indicative of the endometrial cancer, or a given prognosis. Furthermore, the degree of change of one or more miRNA level(s) can be related to the severity of the cancer or cancer progression.

In one embodiment, an in vitro method for identifying a test therapeutic agent to inhibit endometrial cancer cells is provided, said method comprising : a) determining the level of expression of at least one miRNA selected from the group consisting of miR10a, miR25, miR28-3p, miR29a, miR30a*, miR30b, miR30e, miR146a, miR146b-5p, miR451, miR660, miR3613-5p and miR4487 prior to contacting the test therapeutic agent with one or more endometrial cancer cells; and b) determining the level of expression of at least one corresponding miRNA in step (a) after contacting the test therapeutic agent with one or more endometrial cancer cells, wherein a decrease level of expression of one of more of the following miRNAs after contacting the test therapeutic agent with one or more endometrial cancer cells relative to the expression level of the corresponding miRNA prior to contacting the test therapeutic agent with one or more endometrial cancer cells, is an indication that the test therapeutic agent is efficacious for inhibiting endometrial cancer: miR10a, miR25, miR28-3p, miR29a, miR30a*, miR30b, miR30e, miR146a, miR146b-5p, miR451 or miR660, and wherein an increase level of expression of one of more of the following miRNAs after contacting the test therapeutic agent with one or more endometrial cancer cells relative to the expression level of the corresponding miRNA prior to contacting the test therapeutic agent with one or more endometrial cancer cells, is an indication that the test therapeutic agent is efficacious for inhibiting endometrial cancer: miR3613-5p or miR4487.

In another embodiment, a method for determining the efficacy of a therapy for inhibiting endometrial cancer cells in a subject is provided, said method comprising the steps of comparing: a) the level of expression of at least one miRNA selected from the group consisting of miR10a, miR25, miR28-3p, miR29a, miR30a*, miR30b, miR30e, miR146a, miR146b-5p, miR451, miR660, miR3613-5p and miR4487 in a first sample obtained from the subject prior to providing at least a portion of the therapy to the subject, and b) the level of expression of at least one corresponding miRNA in step (a) in a second sample obtained from the subject after providing at least a portion of the therapy to the subject, wherein a decrease level of expression of one of more of the following miRNAs in the second sample relative to the expression level of the corresponding miRNA in the first sample, is an indication that the therapy is efficacious for inhibiting endometrial cancer: miR10a, miR25, miR28-3p, miR29a, miR30a*, miR30b, miR30e, miR146a, miR146b-5p, miR451 or miR660, and wherein an increase level of expression of one of more of the following miRNAs in the second sample relative to the expression level of the corresponding miRNA in the first sample, is an indication that the therapy is efficacious for inhibiting endometrial cancer: miR3613-5p or miR4487.

In one embodiment, the kit comprises at least one agent for sequencing or measuring the expression level of at least one miRNA selected from the group consisting of: miR10a, miR25, miR28-3p, miR29a, miR30a*, miR30b, miR30e, miR146a, miR146b-5p, miR451 and miR660 in a sample of a subject in need of a diagnosis of or predicting the risk of developing endometrial cancer.

In another embodiment, the kit comprises at least two agents for sequencing or measuring the expression level of at least two miRNAs selected from the group consisting of MiR21, miR283p, miR29a, miR141, miR200a, miR200b, miR 451, and miR660 in a sample of a subject in need of a diagnosis of or predicting the risk of developing endometrial cancer.

In yet another embodiment, the kit further comprises an instruction for use of the kit to diagnose or evaluate the risk of developing endometrial cancer.

In an exemplary embodiment, the agent is RT-PCR. In another exemplary embodiment, the kit comprises at least one miRNA-specific oligonucleotide probe that is at least 90%, 91%, 92%, 93%, 94%, 95%, 96%, 97%, 98%, 99% or 100% identical to a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO:17.

"Identical" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

Methods for detecting endometrial cancer in a subject are provided, comprising the step of measuring the expression level of at least one of the following miRNA in the test sample of the subject: miR10a, miR25, miR28-3p, miR29a, miR30a*, miR30b, miR30e, miR146a, miR146b-5p, miR451, miR660, miR3613-5p and miR4487 in the test sample of the subject, where in a higher expression level of at least one of the following miRNA in the test sample, relative to the expression level of at least one corresponding miRNA in an endometrial cancer-free sample, is indicative of the subject having endometrial cancer or has a risk of developing endometrial cancer: miR10a, miR25, miR28-3p, miR29a, miR30a*, miR30b, miR30e, miR146a, miR146b-5p, miR451 or miR660, and where in a lower expression level of at least one of the following miRNA in the test sample, relative to the expression level of at least one corresponding miRNA in an endometrial cancer-free sample, is indicative of the subject having endometrial cancer or has a risk of developing endometrial cancer: miR-3613-5P or miR4487.

Also provided are methods for detecting endometrial cancer in a subject, comprising the step of measuring the expression level of at least two of the following miRNAs in the test sample of the subject: MiR21, miR283p, miR29a, miR141, miR200a, miR200b, miR 451, or miR660, wherein a higher expression level of at least two of the miRNAs in the test sample, relative to the expression level of the corresponding two miRNA in an endometrial cancer-free sample, is indicative of the subject having endometrial cancer. In one embodiment, the method comprises measuring the expression level of a first miRNA and a second miRNA, wherein the first miRNA is miR660 and the second miRNA is miR451 or miR29a. In another embodiment, the first miRNA is miR451 and the second miRNA is miR 21, miR 28-3p, miR141, miR200a or miR200b. In yet another embodiment, the first miRNA is miR200b and the second miRNA is miR21, miR28-3 miR29a or miR141. In yet another embodiment, the first miRNA is miR141 and the second miRNA is miR29a. In yet another embodiment, the first miRNA is miR28-3p and the second miRNA is miR21.

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Description of Materials and Methods Used in the Examples

Study Participant: A case control study was conducted to examine the expression of various miRNAs in patients with a history of endometrial simple or complex hyperplasia without atypia (SH/CH-nonA) who developed endometrial cancer (case) and who did not developed endometrial cancer (control). This research protocol was approved by the Institutional Review Board of the Chang Gung Memorial Hospital, Taiwan (IRB #100-4355A3).

The case group were identified in Chang Gung Memorial Hospital cancer database as those who had a history of SH or CH-nonA and subsequently developed endometrial cancer (EC) (n=9, see Table 1). The patients in the controlled group were prospectively enrolled when they underwent hysteroscopic resection of endometrial lesions with proven SH or CH-nonA lesion but did not progress to endometrial cancer after at least four years of follow up (n=27) (Table 2). Serum drawn from healthy donors was obtained from the tissue bank of Chang Gung Memorial Hospital also served as normal control. Serum and tissue were collected from endometrial cancer cases prospectively from 2012 to 2016 as test set. Two pathologists (RCW and SMJ) independently reviewed all histology slides and any discrepancies were resolved by consensus. Clinical information of patients was retrieved from the electronic medical records informatics system of Chang Gung Memorial Hospital, Taiwan.

TABLE 1

Demographics and patients with history of SH/CH without atypia and subsequently developed Endometrial cancer (SH/CH-nonA preceded EC cases)

| Study code | Date of SH diagnosis | SH/CH Diagnosis | Date of EC diagnosis | Histological Diagnosis | Age at EC Diagnosis | Stage | Grade |
|---|---|---|---|---|---|---|---|
| SH-01P | 1989 Apr. 13 | Focal polypoid. Hyperplasia | 2004 May 11 | endometrioid | 64 | IIIC | 3 |
| SH-02P | 1998 Apr. 27 | SH | 2004 Feb. 27 | endometrioid | 44 | IB | 2 |
| SH-03P | 2000 Oct. 9 | simple EH | 2003 Aug. 23 | endometrioid | 50 | IA | 1 |
| SH-06P | 2008 Sep. 26 | Adenomatous. Hyperplasia | 2009 Apr. 14 | Endometrioid | 42 | IA | 1 |
| SH-07P | 1992 Nov. 20 | complex hyperplasia | 2005 Aug. 23 | Endometrioid | 58 | IB | 2 |
| SH-08P | 2008 Aug. 26 | SH | 2012 Apr. 24 | Endometrioid | 53 | IA | 2 |
| SH-012P | 2001 Oct. 29 | SH and CH without atypia | 2009 Jun. 15 | Endometrioid | 39 | IA | 1 |
| SH-013P | 2005 Jul. 6 | SH without atypia | 2015 Sep. 8 | Endometrioid | 55 | IA | 1 |
| SH-014P | 2011 Apr. 1 | SH without atypia | 2015 May 26 | Endometrioid | 42 | IA | 1 |

TABLE 2

Demographics and patients with history of SH/CH without atypia but did not progress to endometrial cancer (SH/CH-nonA controls)

| Study code | Diagnosis |
|---|---|
| SH-C01 | simple hyperplasia without atypia |
| SH-C02 | simple hyperplasia without atypia |
| SH-C03 | simple hyperplasia without atypia |
| SH-C04 | simple hyperplasia without atypia |
| SH-C05 | simple hyperplasia with focal complex hyperplasia |
| SH-C07 | mild simple hyperplasia without atypia |
| SH-C08 | simple hyperplasia without atypia |
| SH-C09 | simple hyperplasia without atypia |
| SH-C10 | simple hyperplasia without atypia |
| SH-C11 | simple hyperplasia with breakdown |
| SH-C12 | mild simple hyperplasia without atypia |
| SH-C13 | simple hyperplasia without atypia |
| SH-C14 | simple hyperplasia without atypia |
| SH-C15 | simple hyperplasia with focal breakdown |
| SH-C16 | simple hyperplasia without atypia |
| SH-C17 | simple hyperplasia without atypia |
| SH-C18 | simple hyperplasia without atypia |
| SH-C19 | simple hyperplasia without atypia |
| SH-C20 | simple hyperplasia/chronic endometritis |
| SH-C21 | secretory with hyperplasia without atypia |
| SH-C22 | simple hyperplasia without atypia |
| SH-C23 | cystic hyperplasia without atypia |
| SH-C24 | simple hyperplasia without atypia |
| SH-C25 | simple hyperplasia with breakdown |
| SH-C27 | endometrial hyperplasia polyp |
| SH-C28 | simple hyperplasia without atypia |
| SH-C29 | simple hyperplasia without atypia |

RNA Extraction from Formalin Fixed Paraffin Embedded (FFPE) Tissue Blocks 5 slices of 10 μm-thick FFPE tissues blocks were selected. Paraffin was removed using deparaffinization solution (QiA-GEN, Germany), followed by RNA extraction and DNase treatment using miRNAeasy FFPE kit (QiAGEN) according to the manufacturer's instructions. RNA is quantified using a Bioanalyzer (Agilent Technology, USA).

MiRNA 3.0 Array and Target Prediction of miRNA

To investigate the differential expressions of miRNAs in the case and control groups, Affymetrix miRNA 3.0 arrays (Thermo Fisher Scientific, USA) with 2578 human mature miRNA probe sets was performed according to the manufacturer's instructions. Briefly, 1 μg of total RNA of each sample was subjected to a tailing reaction labeled with the Flashtag RNA labeling kit (Genisphere, USA) followed by ligation of the biotinylated signal molecule to the RNA sample according to the manufacturer's instructions. Each sample was hybridized to a 3.0 miRNA Array at 48° C. for 16 h and then washed and stained on a Fluidics Station 450. After staining, the chip was scanned by GeneChip Scanner 3000 7G (Thermo Fisher Scientific). Expression levels of miRNA transcripts was captured through the probe set by Command Console 3.2 (Affymetrix, USA). Affymetrix® Transcriptome Analysis Console Software (TAC) was downloaded for free to analyse miRNA 3.0 array and miRbase (http://www.mirbase.org) was used to identify potential target sites of miRNA.

Serum RNA Extraction

Total RNA was isolated using Trizol reagent. Briefly, 250 uL of serum sample was mixed with 750 uL of Trizol reagent and 200 ul of chloroform. One microliter of 0.05 nM synthetic Caenorhabditis elegans-specific microRNA cel-miR-39 was added to each serum specimen as the spike-in control. RNA was purified following the manufacture's protocol and dissolved in 15 uL of RNase-free water.

Reverse Transcription

The RNA extracted from the FFPE tissue (350 ng) or serum (4.0 μL each) were subjected to reverse transcription (RT) using a TaqMan miRNA Reverse Transcription Kit and TaqMan® MicroRNA Assays (Applied Biosystems, USA) according to the manufacturer's protocol. Briefly, RT primers corresponding to the miRNAs from TaqMan® MicroRNA Assays (Applied Biosystems) were mixed together to convert the miRNAs into their corresponding cDNAs in a single reaction, and individual PCR was performed using the following cycling conditions: 16° C. for 30 min, followed by 42° C. for 30 min and 85° C. for 5 min. The products were diluted with 0.1× TE buffer prior to quantitative PCR (qPCR).

Quantitative Real-Time PCR

The real-time quantitative reverse transcription PCR (qRT-PCR) was used to determine the expression levels of miR in FFPE tissues or serum. The TaqMan MicroRNA Assay (Applied Biosystems) was used to prepare the samples. The expression levels of miR16 and cel-miR39 were used as internal control for tissue and serum, respectively. The real-time PCR amplification conditions were as follows: initial denaturation for 10 min at 95° C., followed by 45 cycles of 95° C. for 15 s and 60° C. for 1 min. The reactions were performed by using the ABI PRISM 7900 HT instrument (Applied Biosystems). A mean cycle of threshold (Ct) value for each duplicate measurement was calculated. The analytical detection limit was defined as a Ct value of 40; miRNAs with Ct>40 were considered undetectable.

Immunohistochemistry

FFPE tissue slices (4-μm thick) were deparaffinized in xylene and rehydrated through a series of graded ethanol baths. The slices were stained with anti-rabbit Phosphatase and tensin homolog (PTEN) monoclonal antibody (Cell Signaling Technology, USA) using an automated IHC stainer with the Ventana Basic DAB Detection kit (Tucson, USA). Counterstaining was performed with hematoxylin. For the PTEN staining, positive stromal cells were regarded as internal positive controls. Portions of the IHC data for both benign and malignant tissues were retrieved from a previous study (Oncotarget, 2017 Aug. 10; 8(43):74434-74450).

Statistical Analysis

Data were analyzed using the following statistical tests and statistical software package: nonparametric Mann-Whitney U test for comparing groups according to continuous variables, Fisher's exact test for the protein expression levels of PTEN in hyperplasia patients, the area under the curves of receiver operating curve analysis for the optimal cutoff values of discovered biomarker(s), and SPSS (version 22, USA). All tests were two-sided, and P values less than 0.05 were considered statistically significant.

Results miRNA Expression Profile by miR Array

As illustrated in the FIG., the miRNA expression profile of FFPE tissues of 6 cases from the case group (i.e., patients with a history of SH or CH-nonA and subsequently developed endometrial cancer) and 12 cases from the control groups (i.e., patients with a history of SH or CH-nonA but did not progress to endometrial cancer after 4 years of follow up) show that 20 miRNAs (P<0.01, fold change >4) were significant different in control groups and case groups. Among those, eighteen miRNAs were significantly overexpressed in the case group (miR10a, miR15a, miR21, miR25, miR28-3p, miR29a, miR30a*, miR30b, miR30e, miR141, miR146a, miR146b-5p, miR181d, miR194, miR200a, miR200b, miR451 and miR660) as compared to the control group and two miRNAs were underexpressed in the case group as compared to the control group (miR-3613-5P or miR4487).

MiRNAs Expression Profile of Another Independent Cohort by TaqMan RT-qPCR

The expression profiles of the 20 miRNAs in the FIG. were further analyzed based on another independent FFPE tissue cohort using multiplex real-time quantitative PCR (RT-qPCR) analysis. The cohort includes 9 patients from the case group with a history of SH and 28 patients from the control group with a history of SH. RT-qPCR analysis shows six miRNA expression levels (miR21, miR30*, miR141, miR200a, miR200b, and miR660) were significantly higher in the case groups than that of control groups (p<0.05), see Table 3.

TABLE 3 miRNAs expression profile of the control group (n = 28) and the case group (n = 9)

| MiR | Fold change (SH-Case/ SH-Control) | P value (Mann-Whitney) | PTEN target |
|---|---|---|---|
| miR21 | 1.66 | P = 0.0338 | PTEN |
| miR30a* | 1.92 | P = 0.003 | — |
| miR141 | 3.13 | P = 0.0004 | PTEN |
| miR200a | 4.00 | P < 0.0001 | PTEN |
| miR200b | 4.32 | P < 0.0001 | PTEN |
| miR660 | 1.58 | P = 0.0392 | — |

— Not reported

PTEN status in hyperplasia tissue sample and association with miRNAs expression

The status of PTEN tumor suppressor in the case group and the control group was investigated. Table 4 shows loss of PTEN expression was in 5 of the 22 control cohort (22.7%) and in 4 of 8 case cohort (50%). The percentage of PTEN loss was significantly higher in the case group compared to that of the control group (22.7% vs 50%, p=0.016).

TABLE 4

The percentage of PTEN loss is significantly higher in the case group than that of the control group.

| Count (%) | PTEN loss | PTEN heterogeneous | PTEN positive | Total |
|---|---|---|---|---|
| Control Cohort (n = 22) | 5 (22.7%) | 2 (9.1%) | 15 (68.2%) | 22 (100%) |
| Case Cohort (n = 8) | 4 (50%) | 3 (37.5%) | 1 (12.5%) | 8 (100%) |

Fisher exact, p = 0.016

Serum miRNA Levels are Increased in Endometrial Cancer Patients

Multiplex RT-qPCR test was performed on the miRNAs using serum samples from the cancer case cohort and healthy control. Table 5 shows the following four miRNAs were overexpressed in the case cohort: miR21, miR141, miR200b, and miR660 and Table 6 shows the sensitivity and specificity of the overexpressed miRNAs in endometrial cancer diagnosis.

TABLE 5

Selected miRNAs with significantly differential expression between cancer case cohort and healthy control

| MiR | Fold change (Cancer Case/ Healthy control) | PTEN target |
|---|---|---|
| miR21 (119 vs 123) | 2.78 | PTEN |
| miR141 (41 vs 79) | 1.62 | PTEN |
| miR200b (94 vs 117) | 2.95 | PTEN |
| miR660 (86 vs 84) | 7.37 | PTEN |

— Not reported

TABLE 6

The sensitivity and specificity of miRNA used in endometrial cancer diagnosis

| MiR | Sensitivity | Specificity |
|---|---|---|
| miR660 | 0.942 | 0.940 |
| miR451 | 0.837 | 0.897 |
| miR200b | 0.719 | 0.694 |
| miR200a | 0.196 | 0.874 |
| miR141 | 0.682 | 0.684 |
| miR29a | 0.714 | 0.882 |
| miR28-3p | 0.750 | 0.613 |
| miR21 | 0.815 | 0.702 |

In addition, the combination of specific miRNA expression profile lead to unexpected synergy in endometrial cancer diagnostic sensitivity or specificity is shown in Table 7.

TABLE 7

Sensitivity and specificity of miRNA combinations

| MiR Combination | Specificity | Sensitivity |
|---|---|---|
| miR660 + miR451 | 0.778 | 1.000 |
| miR660 + miR200b | 0.841 | 0.933 |
| miR660 + miR200a | 0.925 | 0.862 |
| miR660 + miR141 | 0.857 | 0.900 |
| miR660 + miR29a | 0.722 | 1.000 |
| miR660 + miR28-3p | 0.941 | 0.894 |
| miR660 + miR21 | 0.971 | 0.909 |
| miR451 + miR200b | 0.676 | 0.923 |
| miR451 + miR200a | 0.690 | 0.909 |
| miR451 + miR141 | 0.667 | 1.000 |
| miR451 + miR29a | 0.837 | 0.897 |
| miR451 + miR28-3p | 0.710 | 0.909 |
| miR451 + miR21 | 0.677 | 1.000 |
| miR200b + miR200a | 0.850 | 0.476 |
| miR200b + miR141 | 0.771 | 0.710 |
| miR200b + miR29a | 0.771 | 0.857 |
| miR200b + miR28-3p | 0.827 | 0.676 |
| miR200b + miR21 | 0.852 | 0.670 |
| miR200a + miR141 | 0.818 | 0.423 |
| miR200a + miR29a | 0.867 | 0.815 |
| miR200a + miR28-3p | 0.696 | 0.504 |
| miR200a + miR21 | 0.821 | 0.517 |
| miR141 + miR29a | 0.875 | 0.897 |
| miR141 + miR28-3p | 0.727 | 0.684 |
| miR141 + miR21 | 0.659 | 0.797 |
| miR29a + miR28-3p | 0.824 | 0.755 |
| miR29a + miR21 | 0.780 | 0.825 |
| miR28-3p + miR21 | 0.832 | 0.610 |

What is claimed is:

1. A method for detecting endometrial cancer or predicting the risk of developing endometrial cancer and treating endometrial cancer in a subject, comprising
   (a) measuring the expression level of at least one miRNA selected from the group consisting of miR28-3p, miR29a, miR 451, miR30a*, miR30b, miR30e, miR3613-5p, miR4487 and miR660 in the test sample of the subject,
   wherein the higher expression level of at least one of the following miRNA, relative to the expression level of at least one corresponding miRNAs in an endometrial cancer-free sample, is indicative of the subject having endometrial cancer or has a risk of developing endometrial cancer: miR660, miR28-3p, miR29a, miR30a*, miR30b, miR30e, or miR451, and
   wherein in a lower expression level of at least one of the following miRNA in the test sample, relative to the expression level of at least one corresponding miRNA in an endometrial cancer-free sample, is indicative of the subject having endometrial cancer or has a risk of developing endometrial cancer: miR-3613-5P or miR4487; and
   (b) administering to the subject in need thereof a therapeutic agent that is efficacious to inhibit endometrial cancer.

2. The method of claim 1, wherein the miRNA expression level is determined by real-time PCR.

3. The method of claim 1, wherein the miRNA expression level is determined by at least one oligonucleotide probe complementary to the miRNAs at least 90% homologous to SEQ ID NO:3, SEQ ID NO: 4, SEQ ID NO:5, SEQ ID NO:6, SEQ ID NO:7, SEQ ID NO:10, SEQ ID NO: 11, SEQ ID NO: 12, or SEQ ID NO:13.

4. The method of claim 1, wherein the subject has a history of endometrial hyperplasia.

5. The method of claim 4, wherein the subject has a history of simple hyperplasia or complex hyperplasia without atypia.

6. The method of claim 1, comprising measuring the expression level of both miR660 and miR451.

7. The method of claim 1, comprising measuring the expression level of both miR660 and miR29a.

8. The method of claim 1, further comprising measuring the expression level of at least one miRNA selected from the group consisting of miR21, miR141, miR200a and miR200b.

* * * * *

SEQUENCE LISTING

```
<160> NUMBER OF SEQ ID NOS: 17

<210> SEQ ID NO 1
<211> LENGTH: 45
<212> TYPE: RNA
<213> ORGANISM: Artificial Sequence
<220> FEATURE:
<223> OTHER INFORMATION: miR10a
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(45)

<400> SEQUENCE: 1
uacccuguag auccgaauuu guguagcuua ucagacugau guuga            45

<210> SEQ ID NO 2
<211> LENGTH: 22
<212> TYPE: RNA
<213> ORGANISM: Artificial Sequence
<220> FEATURE:
<223> OTHER INFORMATION: miR25
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 2
cauugcacuu gucucggucu ga                                    22

<210> SEQ ID NO 3
<211> LENGTH: 22
<212> TYPE: RNA
```

-continued

```
<213> ORGANISM: Artificial Sequence
<220> FEATURE:
<223> OTHER INFORMATION: miR28-3p
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 3
cacuagauug ugagcuccug ga                                              22

<210> SEQ ID NO 4
<211> LENGTH: 22
<212> TYPE: RNA
<213> ORGANISM: Artificial Sequence
<220> FEATURE:
<223> OTHER INFORMATION: miR29a
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 4
uagcaccauc ugaaaucggu ua                                              22

<210> SEQ ID NO 5
<211> LENGTH: 22
<212> TYPE: RNA
<213> ORGANISM: Artificial Sequence
<220> FEATURE:
<223> OTHER INFORMATION: miR30a*
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 5
cuuucagucg gauguuugca gc                                              22

<210> SEQ ID NO 6
<211> LENGTH: 22
<212> TYPE: RNA
<213> ORGANISM: Artificial Sequence
<220> FEATURE:
<223> OTHER INFORMATION: miR30b
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 6
uguaaacauc cuacacucag cu                                              22

<210> SEQ ID NO 7
<211> LENGTH: 22
<212> TYPE: RNA
<213> ORGANISM: Artificial Sequence
<220> FEATURE:
<223> OTHER INFORMATION: miR30e
```

```
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 7
uguaaacauc cuugacugga ag                                          22

<210> SEQ ID NO 8
<211> LENGTH: 22
<212> TYPE: RNA
<213> ORGANISM: Artificial Sequence
<220> FEATURE:
<223> OTHER INFORMATION: miR146a
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 8
ugagaacuga auuccauggg uu                                          22

<210> SEQ ID NO 9
<211> LENGTH: 22
<212> TYPE: RNA
<213> ORGANISM: Artificial Sequence
<220> FEATURE:
<223> OTHER INFORMATION: miR146b-5p
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 9
ugagaacuga auuccauagg cu                                          22

<210> SEQ ID NO 10
<211> LENGTH: 22
<212> TYPE: RNA
<213> ORGANISM: Artificial Sequence
<220> FEATURE:
<223> OTHER INFORMATION: miR451
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 10
aaaccguuac cauuacugag uu                                          22

<210> SEQ ID NO 11
<211> LENGTH: 22
<212> TYPE: RNA
<213> ORGANISM: Artificial Sequence
<220> FEATURE:
<223> OTHER INFORMATION: miR660
<300> PUBLICATION INFORMATION:
<302> TITLE: 123
<308> DATABASE ACCESSION NUMBER: 123
```

```
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 11
uacccauugc auaucggagu ug                                              22

<210> SEQ ID NO 12
<211> LENGTH: 22
<212> TYPE: RNA
<213> ORGANISM: Artificial Sequence
<220> FEATURE:
<223> OTHER INFORMATION: miR3613-5p
<300> PUBLICATION INFORMATION:
<302> TITLE: 123
<308> DATABASE ACCESSION NUMBER: 123
<309> DATABASE ENTRY DATE: 2018-01-01
<310> PATENT DOCUMENT NUMBER: 123
<311> PATENT FILING DATE: 2018-01-02
<313> RELEVANT RESIDUES IN SEQ ID NO: (1)..(22)

<400> SEQUENCE: 12
uguuguacuu uuuuuuugu uc                                               22

<210> SEQ ID NO 13
<211> LENGTH: 19
<212> TYPE: RNA
<213> ORGANISM: Artificial Sequence
<220> FEATURE:
<223> OTHER INFORMATION: miR4487

<400> SEQUENCE: 13
agagcuggcu gaagggcag                                                  19

<210> SEQ ID NO 14
<211> LENGTH: 22
<212> TYPE: RNA
<213> ORGANISM: Artificial Sequence
<220> FEATURE:
<223> OTHER INFORMATION: miR21

<400> SEQUENCE: 14
uagcuuauca gacugauguu ga                                              22

<210> SEQ ID NO 15
<211> LENGTH: 22
<212> TYPE: RNA
<213> ORGANISM: Artificial Sequence
<220> FEATURE:
<223> OTHER INFORMATION: miR141

<400> SEQUENCE: 15
uaacacuguc ugguaaagau gg                                              22

<210> SEQ ID NO 16
<211> LENGTH: 22
<212> TYPE: RNA
<213> ORGANISM: Artificial Sequence
<220> FEATURE:
<223> OTHER INFORMATION: miR200a

<400> SEQUENCE: 16
uaacacuguc ugguaacgau gu                                              22

<210> SEQ ID NO 17
<211> LENGTH: 22
```

```
<212> TYPE: RNA
<213> ORGANISM: Artificial Sequence
<220> FEATURE:
<223> OTHER INFORMATION: miR200b

<400> SEQUENCE: 17
uaauacugcc ugguaaugau ga                                              22
```